(12) United States Patent
Smith et al.

(10) Patent No.: US 8,917,184 B2
(45) Date of Patent: Dec. 23, 2014

(54) ANALYTE TESTING METHOD AND SYSTEM

(75) Inventors: Antony Smith, Dingwall (GB); Alistair Longmuir, Moray (GB); Allan Faulkner, Avoch (GB)

(73) Assignee: Lifescan Scotland Limited, Inverness (GB)

( * ) Notice: Subject to any disclaimer, the term of this patent is extended or adjusted under 35 U.S.C. 154(b) by 916 days.

(21) Appl. No.: 12/408,613

(22) Filed: Mar. 20, 2009

(65) Prior Publication Data
US 2009/0237262 A1 Sep. 24, 2009

Related U.S. Application Data

(60) Provisional application No. 61/038,624, filed on Mar. 21, 2008.

(51) Int. Cl.
| | |
|---|---|
| G08B 21/00 | (2006.01) |
| G06F 19/00 | (2011.01) |
| H04N 21/472 | (2011.01) |
| G06F 3/023 | (2006.01) |
| A61B 5/145 | (2006.01) |
| H04N 21/485 | (2011.01) |
| H04N 21/482 | (2011.01) |

(52) U.S. Cl.
CPC .......... *G06F 19/3406* (2013.01); *H04N 21/472* (2013.01); *G06F 3/023* (2013.01); *A61B 5/14532* (2013.01); *G06F 19/3456* (2013.01); *A61B 2562/0295* (2013.01); *H04N 21/485* (2013.01); *H04N 21/482* (2013.01)
USPC ............ 340/635; 340/309.7; 436/14; 436/95; 436/149; 600/347; 600/345; 600/583

(58) Field of Classification Search
CPC ............. G08F 19/3406; H04N 21/482; H04N 21/485; H04N 21/472; G06F 3/023; G06F 19/3456; A61B 5/14532; A61B 2562/0295
USPC ........... 340/635, 309.7; 436/14, 95, 149, 150, 436/164; 422/58, 57; 600/347, 345, 583; 73/64.56
See application file for complete search history.

(56) References Cited

U.S. PATENT DOCUMENTS

| | | | |
|---|---|---|---|
| 4,970,172 | A | 11/1990 | Kundu |
| 5,019,974 | A | 5/1991 | Beckers |

(Continued)

FOREIGN PATENT DOCUMENTS

| | | | |
|---|---|---|---|
| CN | 1472536 A | 2/2004 | |
| CN | 1871576 A | 11/2006 | |

(Continued)

OTHER PUBLICATIONS

European Search Report, Netherlands, Jul. 31, 2009, re Application 09250775.5.

(Continued)

*Primary Examiner* — Hoi Lau

(57) ABSTRACT

Various systems and methods of operating an analyte measurement device is provided. The device has a display, user interface, processor, memory and user interface buttons. In one example, one of the methods can be achieved by measuring an analyte with the analyte measurement device; displaying a value representative of the analyte; prompting a user to activate a test reminder; and activating the test reminder to remind a user to conduct a test measurement at a different time. Other methods and systems are also described and illustrated.

15 Claims, 13 Drawing Sheets

(56) References Cited

U.S. PATENT DOCUMENTS

| | | |
|---|---|---|
| 5,071,769 A | 12/1991 | Kundu et al. |
| 5,077,476 A | 12/1991 | Rosenthal |
| 5,086,229 A | 2/1992 | Rosenthal et al. |
| 5,174,959 A | 12/1992 | Kundu et al. |
| 5,216,597 A | 6/1993 | Beckers |
| 5,307,263 A | 4/1994 | Brown |
| 5,410,474 A | 4/1995 | Fox |
| 5,494,562 A | 2/1996 | Maley et al. |
| 5,529,676 A | 6/1996 | Maley et al. |
| 5,573,647 A | 11/1996 | Maley et al. |
| 5,582,698 A | 12/1996 | Flaherty et al. |
| 5,601,694 A | 2/1997 | Maley et al. |
| 5,616,222 A | 4/1997 | Maley et al. |
| 5,665,215 A | 9/1997 | Bussmann et al. |
| 5,695,623 A | 12/1997 | Michel et al. |
| 5,707,502 A | 1/1998 | McCaffrey et al. |
| 5,708,247 A | 1/1998 | McAleer et al. |
| 5,711,868 A | 1/1998 | Maley et al. |
| 5,770,028 A | 6/1998 | Maley et al. |
| 5,899,855 A | 5/1999 | Brown |
| 5,951,836 A | 9/1999 | McAleer et al. |
| 5,997,475 A | 12/1999 | Bortz |
| 6,033,866 A | 3/2000 | Guo et al. |
| 6,040,195 A | 3/2000 | Carroll et al. |
| 6,060,327 A | 5/2000 | Keen |
| 6,136,610 A | 10/2000 | Polito et al. |
| 6,168,563 B1 | 1/2001 | Brown |
| 6,241,862 B1 | 6/2001 | McAleer et al. |
| 6,246,966 B1 | 6/2001 | Perry |
| 6,284,550 B1 | 9/2001 | Carroll et al. |
| 6,326,215 B1 | 12/2001 | Keen |
| D456,083 S | 4/2002 | Clark et al. |
| D456,910 S | 5/2002 | Clark et al. |
| 6,461,331 B1 | 10/2002 | Van Antwerp |
| 6,475,372 B1 | 11/2002 | Ohara et al. |
| D469,107 S | 1/2003 | Miller et al. |
| 6,513,532 B2 | 2/2003 | Mault et al. |
| 6,514,460 B1 | 2/2003 | Fendrock |
| 6,562,625 B2 | 5/2003 | Modzelewski et al. |
| 6,604,050 B2 | 8/2003 | Trippel et al. |
| 6,633,772 B2 | 10/2003 | Ford et al. |
| 6,635,014 B2 | 10/2003 | Starkweather et al. |
| 6,645,368 B1 | 11/2003 | Beaty et al. |
| 6,656,114 B1 | 12/2003 | Poulsen et al. |
| 6,685,651 B2 * | 2/2004 | Anker et al. ............. 600/551 |
| 6,699,667 B2 | 3/2004 | Keen |
| 6,716,577 B1 | 4/2004 | Yu et al. |
| 6,726,818 B2 | 4/2004 | Cui et al. |
| 6,733,655 B1 | 5/2004 | Davies et al. |
| 6,736,957 B1 | 5/2004 | Forrow et al. |
| 6,743,635 B2 | 6/2004 | Neel et al. |
| 6,744,350 B2 | 6/2004 | Blomquist |
| 6,767,441 B1 | 7/2004 | Cai et al. |
| 6,780,645 B2 | 8/2004 | Hayter et al. |
| 6,809,507 B2 | 10/2004 | Morgan et al. |
| 6,810,290 B2 | 10/2004 | Lebel et al. |
| 6,852,104 B2 * | 2/2005 | Blomquist ............. 604/504 |
| 6,872,299 B2 | 3/2005 | Kermani et al. |
| 6,890,421 B2 | 5/2005 | Ohara et al. |
| 6,939,450 B2 | 9/2005 | Karinka et al. |
| 6,942,769 B2 | 9/2005 | Cheng et al. |
| 6,946,299 B2 | 9/2005 | Neel et al. |
| 6,953,693 B2 | 10/2005 | Neel et al. |
| 6,959,247 B2 | 10/2005 | Neel et al. |
| 6,964,871 B2 | 11/2005 | Bell et al. |
| 6,979,544 B2 | 12/2005 | Keen |
| 6,991,940 B2 | 1/2006 | Carroll et al. |
| 6,997,344 B2 * | 2/2006 | Brown et al. ............. 221/258 |
| 7,022,072 B2 | 4/2006 | Fox et al. |
| 7,024,236 B2 | 4/2006 | Ford et al. |
| 7,037,196 B2 | 5/2006 | Kobayashi et al. |
| 7,039,878 B2 | 5/2006 | Auer et al. |
| 7,049,130 B2 | 5/2006 | Carroll et al. |
| 7,054,823 B1 | 5/2006 | Briegs et al. |
| 7,086,277 B2 | 8/2006 | Tess et al. |
| 7,112,265 B1 | 9/2006 | McAleer et al. |
| 7,160,251 B2 | 1/2007 | Neel et al. |
| 7,163,616 B2 | 1/2007 | Vreeke et al. |
| 7,179,226 B2 | 2/2007 | Crothall et al. |
| 7,204,823 B2 | 4/2007 | Estes et al. |
| D542,681 S | 5/2007 | Young et al. |
| 7,212,399 B2 | 5/2007 | Kee et al. |
| 7,220,550 B2 | 5/2007 | Keen |
| 7,223,235 B2 | 5/2007 | Brown et al. |
| 7,223,236 B2 | 5/2007 | Brown et al. |
| D545,705 S | 7/2007 | Voege |
| 7,241,265 B2 | 7/2007 | Cummings et al. |
| 7,250,105 B1 | 7/2007 | Davies et al. |
| 7,251,514 B2 | 7/2007 | Cho et al. |
| 7,256,714 B2 | 8/2007 | Philipp et al. |
| 7,258,666 B2 | 8/2007 | Brown et al. |
| 7,258,769 B2 | 8/2007 | Cui et al. |
| 7,264,591 B2 | 9/2007 | Brown et al. |
| 7,276,146 B2 | 10/2007 | Wilsey |
| 7,276,147 B2 | 10/2007 | Wilsey |
| 7,288,174 B2 | 10/2007 | Cui et al. |
| 7,291,256 B2 | 11/2007 | Teodorczyk et al. |
| 7,311,812 B2 | 12/2007 | Forrow et al. |
| 7,323,141 B2 * | 1/2008 | Kirchhevel et al. ......... 422/68.1 |
| 7,338,639 B2 | 3/2008 | Burke et al. |
| 7,399,277 B2 | 7/2008 | Saidara et al. |
| 7,611,899 B2 * | 11/2009 | Whitson et al. ............. 436/45 |
| 7,695,677 B2 * | 4/2010 | Werner et al. ............. 422/403 |
| 7,885,146 B2 * | 2/2011 | Parkinson et al. ........... 368/109 |
| 7,906,336 B2 * | 3/2011 | Whitson et al. ............. 436/45 |
| 2001/0011224 A1 | 8/2001 | Brown |
| 2001/0056328 A1 | 12/2001 | Trippel et al. |
| 2002/0047867 A1 | 4/2002 | Mault et al. |
| 2002/0068157 A1 | 6/2002 | Wischerhoff |
| 2002/0109600 A1 | 8/2002 | Mault et al. |
| 2003/0021729 A1 | 1/2003 | Mollet et al. |
| 2003/0032190 A1 | 2/2003 | Brown et al. |
| 2003/0032867 A1 | 2/2003 | Crothall et al. |
| 2003/0032868 A1 | 2/2003 | Graskov et al. |
| 2003/0055406 A1 | 3/2003 | Lebel et al. |
| 2003/0060765 A1 | 3/2003 | Campbell et al. |
| 2003/0065308 A1 | 4/2003 | Lebel et al. |
| 2003/0111357 A1 | 6/2003 | Black |
| 2003/0125612 A1 | 7/2003 | Fox et al. |
| 2003/0163088 A1 * | 8/2003 | Blomquist ............. 604/131 |
| 2003/0163223 A1 * | 8/2003 | Blomquist ............. 700/282 |
| 2003/0203498 A1 | 10/2003 | Neel et al. |
| 2003/0208113 A1 | 11/2003 | Mault et al. |
| 2003/0211617 A1 * | 11/2003 | Jones ............. 436/14 |
| 2003/0212379 A1 * | 11/2003 | Bylund et al. ............. 604/504 |
| 2004/0015102 A1 | 1/2004 | Cummings et al. |
| 2004/0038411 A1 | 2/2004 | Hayter et al. |
| 2004/0039255 A1 | 2/2004 | Simonsen et al. |
| 2004/0048394 A1 * | 3/2004 | Kirchhevel ............. 436/183 |
| 2004/0057340 A1 | 3/2004 | Charles-Erickson et al. |
| 2004/0058433 A1 | 3/2004 | Yu et al. |
| 2004/0059201 A1 | 3/2004 | Ginsberg |
| 2004/0069793 A1 | 4/2004 | Brown et al. |
| 2004/0079653 A1 | 4/2004 | Karinka et al. |
| 2004/0094432 A1 | 5/2004 | Neel et al. |
| 2004/0094433 A1 | 5/2004 | Neel et al. |
| 2004/0096991 A1 | 5/2004 | Zhang |
| 2004/0099540 A1 | 5/2004 | Neel et al. |
| 2004/0104131 A1 | 6/2004 | Neel et al. |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0118704 A1 | 6/2004 | Wang et al. |
| 2004/0153585 A1 | 8/2004 | Kawatahara et al. |
| 2004/0157337 A1 | 8/2004 | Burke et al. |
| 2004/0157339 A1 | 8/2004 | Nurke et al. |
| 2004/0172284 A1 | 9/2004 | Sullivan et al. |
| 2004/0182703 A1 | 9/2004 | Bell et al. |
| 2004/0197935 A1 | 10/2004 | Forrow et al. |
| 2004/0199409 A1 | 10/2004 | Brown |
| 2004/0217019 A1 | 11/2004 | Cai et al. |

(56) References Cited

U.S. PATENT DOCUMENTS

| | | |
|---|---|---|
| 2004/0219694 A1 | 11/2004 | Chittock et al. |
| 2004/0223877 A1 | 11/2004 | Kim et al. |
| 2004/0259180 A1 | 12/2004 | Burke et al. |
| 2005/0009126 A1 | 1/2005 | Andrews et al. |
| 2005/0019848 A1 | 1/2005 | Lee et al. |
| 2005/0033603 A1 | 2/2005 | Suzuki et al. |
| 2005/0038332 A1 | 2/2005 | Saidara et al. |
| 2005/0045476 A1 | 3/2005 | Neel et al. |
| 2005/0049179 A1 | 3/2005 | Davidson et al. |
| 2005/0056539 A1 | 3/2005 | Morgan et al. |
| 2005/0059895 A1 | 3/2005 | Brown |
| 2005/0065760 A1 | 3/2005 | Murtfeldt et al. |
| 2005/0067277 A1 | 3/2005 | Pierce et al. |
| 2005/0074368 A1 | 4/2005 | Moller et al. |
| 2005/0080652 A1 | 4/2005 | Brown |
| 2005/0086083 A1 | 4/2005 | Brown |
| 2005/0109618 A1 | 5/2005 | Davies |
| 2005/0116820 A1* | 6/2005 | Goldreich .............. 340/539.12 |
| 2005/0133368 A1 | 6/2005 | Davies et al. |
| 2005/0137530 A1 | 6/2005 | Campbell et al. |
| 2005/0139469 A1 | 6/2005 | Davies et al. |
| 2005/0143675 A1 | 6/2005 | Neel et al. |
| 2005/0143864 A1 | 6/2005 | Blomquist |
| 2005/0161344 A1 | 7/2005 | Kermani et al. |
| 2005/0163657 A1 | 7/2005 | Childers et al. |
| 2005/0176153 A1 | 8/2005 | O'hara et al. |
| 2005/0183965 A1 | 8/2005 | Davies et al. |
| 2005/0187442 A1 | 8/2005 | Cho et al. |
| 2005/0192492 A1 | 9/2005 | Cho et al. |
| 2005/0197553 A1 | 9/2005 | Cooper |
| 2005/0227370 A1 | 10/2005 | Ramel et al. |
| 2005/0239156 A1 | 10/2005 | Drucker et al. |
| 2005/0240119 A1 | 10/2005 | Draudt et al. |
| 2005/0240444 A1 | 10/2005 | Wooten et al. |
| 2005/0245904 A1 | 11/2005 | Estes et al. |
| 2005/0256739 A1 | 11/2005 | Brown |
| 2005/0260769 A1 | 11/2005 | Jonsson et al. |
| 2005/0287499 A1 | 12/2005 | Yeager |
| 2006/0004611 A1 | 1/2006 | Brown |
| 2006/0009705 A1 | 1/2006 | Brown |
| 2006/0009706 A1 | 1/2006 | Brown |
| 2006/0010014 A1 | 1/2006 | Brown |
| 2006/0030759 A1 | 2/2006 | Weiner et al. |
| 2006/0064035 A1 | 3/2006 | Wang et al. |
| 2006/0080152 A1 | 4/2006 | Brown |
| 2006/0100910 A1 | 5/2006 | Brown |
| 2006/0132292 A1 | 6/2006 | Blomquist |
| 2006/0144704 A1 | 7/2006 | Ghesquiere et al. |
| 2006/0178914 A1 | 8/2006 | Brown |
| 2006/0191787 A1 | 8/2006 | Wang et al. |
| 2006/0201805 A1 | 9/2006 | Forrow et al. |
| 2006/0229502 A1 | 10/2006 | Pollock et al. |
| 2006/0231421 A1 | 10/2006 | Diamond et al. |
| 2006/0231423 A1 | 10/2006 | Harding et al. |
| 2006/0247951 A1 | 11/2006 | Brown |
| 2006/0260940 A1 | 11/2006 | McAleer et al. |
| 2006/0279431 A1 | 12/2006 | Bakarania et al. |
| 2006/0286620 A1* | 12/2006 | Werner et al. ................... 435/14 |
| 2007/0028186 A1* | 2/2007 | Park et al. ..................... 715/810 |
| 2007/0048878 A1 | 3/2007 | Carroll et al. |
| 2007/0061167 A1 | 3/2007 | Brown |
| 2007/0065342 A1 | 3/2007 | Brown et al. |
| 2007/0087397 A1 | 4/2007 | Kraft et al. |
| 2007/0088269 A1* | 4/2007 | Valego et al. ................. 604/151 |
| 2007/0094049 A1 | 4/2007 | Brown |
| 2007/0100665 A1 | 5/2007 | Brown |
| 2007/0118403 A1 | 5/2007 | Brown |
| 2007/0118404 A1 | 5/2007 | Brown |
| 2007/0118588 A1 | 5/2007 | Brown |
| 2007/0118589 A1 | 5/2007 | Brown |
| 2007/0167693 A1 | 7/2007 | Scholler et al. |
| 2007/0170054 A2 | 7/2007 | Wilsey |
| 2007/0170055 A2 | 7/2007 | Wilsey |
| 2007/0179352 A1 | 8/2007 | Randlov et al. |
| 2007/0188349 A1* | 8/2007 | Staniszewski ............ 340/932.2 |
| 2007/0200734 A1* | 8/2007 | Lee et al. ......................... 341/22 |
| 2007/0213603 A1 | 9/2007 | Brown |
| 2007/0213604 A1 | 9/2007 | Brown |
| 2007/0213605 A1 | 9/2007 | Brown |
| 2007/0213608 A1 | 9/2007 | Brown |
| 2007/0218543 A1 | 9/2007 | Flaherty et al. |
| 2007/0230155 A1 | 10/2007 | Christol et al. |
| 2007/0231209 A1 | 10/2007 | Cosentino et al. |
| 2007/0231846 A1 | 10/2007 | Cosentino et al. |
| 2007/0255114 A1 | 11/2007 | Ackermann et al. |
| 2007/0255123 A1 | 11/2007 | Cummings et al. |
| 2007/0255126 A1 | 11/2007 | Moberg et al. |
| 2007/0266871 A1 | 11/2007 | Wegner et al. |
| 2007/0276209 A1 | 11/2007 | Emoto et al. |
| 2007/0276621 A1 | 11/2007 | Davies et al. |
| 2007/0281321 A1 | 12/2007 | Nagale et al. |
| 2007/0287895 A1 | 12/2007 | Brown |
| 2007/0287985 A1 | 12/2007 | Estes et al. |
| 2007/0289881 A1 | 12/2007 | Forrow et al. |
| 2007/0299321 A1 | 12/2007 | Brown |
| 2008/0011059 A1 | 1/2008 | Davies et al. |
| 2008/0023326 A1 | 1/2008 | Forrow et al. |
| 2008/0026473 A1 | 1/2008 | Wang et al. |
| 2008/0032407 A1* | 2/2008 | Brown ............................. 436/46 |
| 2008/0035478 A1 | 2/2008 | Wegner et al. |
| 2008/0073207 A1 | 3/2008 | Teodorczyk et al. |
| 2008/0075143 A1* | 3/2008 | Lampke-Honeyghan et al. ............................. 374/164 |
| 2008/0103447 A1* | 5/2008 | Reggiardo et al. ............ 604/131 |
| 2008/0106431 A1* | 5/2008 | Blomquist ................ 340/825.19 |
| 2008/0114228 A1 | 5/2008 | McCluskey et al. |
| 2008/0118401 A1* | 5/2008 | Kirchhevel et al. .......... 422/68.1 |
| 2008/0119702 A1* | 5/2008 | Reggiardo ..................... 600/345 |
| 2008/0119710 A1* | 5/2008 | Reggiardo et al. ........... 600/365 |
| 2008/0133059 A1* | 6/2008 | Trippel et al. ................. 700/267 |
| 2008/0171967 A1* | 7/2008 | Blomquist et al. .............. 604/67 |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1* | 7/2008 | Blomquist ..................... 604/500 |
| 2008/0177149 A1 | 7/2008 | Weinert et al. |
| 2008/0177822 A1* | 7/2008 | Yoneda .......................... 709/202 |
| 2008/0194934 A1 | 8/2008 | Ray et al. |
| 2008/0257020 A1* | 10/2008 | Jung et al. ..................... 73/64.56 |
| 2008/0294024 A1* | 11/2008 | Cosentino et al. ............ 600/309 |
| 2008/0318624 A1* | 12/2008 | Hedtke et al. ................ 455/556.1 |
| 2009/0051823 A1* | 2/2009 | Tsurumoto et al. ........... 348/734 |
| 2009/0062664 A1* | 3/2009 | Chang et al. .................. 600/485 |
| 2009/0156923 A1* | 6/2009 | Power et al. ................... 600/365 |
| 2009/0171482 A1* | 7/2009 | Mindeman et al. ............. 700/83 |
| 2009/0187351 A1* | 7/2009 | Orr et al. ......................... 702/19 |
| 2009/0227855 A1* | 9/2009 | Hill et al. ...................... 600/365 |
| 2009/0240127 A1* | 9/2009 | Ray ................................. 600/365 |
| 2009/0326355 A1* | 12/2009 | Brenneman et al. .......... 600/347 |
| 2010/0033138 A1 | 2/2010 | Alger et al. |
| 2010/0041084 A1* | 2/2010 | Stephens et al. ............... 435/14 |
| 2010/0069730 A1* | 3/2010 | Bergstrom et al. ........... 600/365 |
| 2011/0263959 A1 | 10/2011 | Young et al. |
| 2012/0189497 A1 | 7/2012 | Jung et al. |

FOREIGN PATENT DOCUMENTS

| | | |
|---|---|---|
| CN | 1917580 A | 2/2007 |
| CN | 101002092 A | 7/2007 |
| CN | 101022762 A | 8/2007 |
| CN | 101137320 A | 3/2008 |
| CN | 101238466 A | 8/2008 |
| DE | 4315532 A1 | 11/1993 |
| EP | 0777123 A | 6/1997 |
| EP | 1369688 A | 12/2003 |
| EP | 1413245 A2 | 4/2004 |
| EP | 1144028 B1 | 6/2004 |
| EP | 1563786 A | 8/2005 |
| EP | 1733677 A1 | 12/2006 |
| EP | 1733678 A1 | 12/2006 |
| EP | 2103251 A1 | 9/2009 |
| GB | 2159625 A | 12/1985 |

(56) References Cited

FOREIGN PATENT DOCUMENTS

| | | |
|---|---|---|
| JP | 2005-237484 | 9/2005 |
| JP | 2008-501426 | 1/2008 |
| JP | 2010-504729 | 2/2010 |
| TW | 200530584 A | 9/2005 |
| WO | WO 94/11831 | 5/1994 |
| WO | 95/24233 A1 | 9/1995 |
| WO | WO 02/24065 | 3/2002 |
| WO | WO 2004/056264 A1 | 7/2004 |
| WO | WO 2005/106446 A1 | 11/2005 |
| WO | WO 2005/121785 A2 | 12/2005 |
| WO | 2006/034104 A1 | 3/2006 |
| WO | 2006/037802 A2 | 4/2006 |
| WO | WO 2006/072035 A | 7/2006 |
| WO | WO 2007/019289 A | 2/2007 |
| WO | WO 2007/019384 A1 | 2/2007 |

OTHER PUBLICATIONS

Chinese Patent Application No. 200910134640.0, Chinese First Office Action dated Jan. 10, 2013, 16 pages, State Intellectual Property Office, P.R. China.

Japanese Patent Application No. 2009-067317, Japanese Notification of Reasons for Refusal dated Jul. 16, 2013, 2 pages.

China Patent Application No. 200910134640.0, Third Office Action, 18 pages, Jan. 23, 2014.

Japanese Patent Application No. 2009-067317, Notification of Reason for Refusal, 3 pages, Dec. 3, 2013.

Taiwan Office Action issued in Taiwan Patent Application No. 98109011, dated Apr. 3, 2014, 9 pages.

English translation of First Search Report issued in corresponding Chinese Patent Application No. 200910134640.0, dated Jan. 5, 2013, 3 pages.

Patent Examination Report No. 1 issued in corresponding Australian Patent application No. 2009201094, dated Jun. 14, 2013, 3 pages.

English translation of Second Office Action issued in corresponding Chinese Patent Application No. 200910134640.0, dated Aug. 22, 2013, 17 pages.

English translation of Fourth Office Action issued in corresponding Chinese Patent Application No. 200910134640.0, dated Jun. 5, 2014, 23 pages.

\* cited by examiner

ANALYTE TESTING METHOD AND SYSTEM

PRIORITY

This application claims the benefits of priority of U.S. Provisional Patent Application Ser. No. 61/038,624 filed on Mar. 21, 2008, which Provisional Patent Application is hereby incorporated by reference into this application.

BACKGROUND

Glucose monitoring is a fact of everyday life for diabetic individuals. The accuracy of such monitoring can significantly affect the health and ultimately the quality of life of the person with diabetes. Generally, a diabetic patient measures blood glucose levels several times a day to monitor and control blood sugar levels. Failure to test blood glucose levels accurately and on a regular basis can result in serious diabetes-related complications, including cardiovascular disease, kidney disease, nerve damage and blindness. There are a number of electronic devices currently available which enable an individual to test the glucose level in a small sample of blood. One such glucose meter is the OneTouch® Profile™ glucose meter, a product which is manufactured by Lifescan Inc.

In addition to glucose monitoring, diabetic individuals often have to maintain tight control over their lifestyle, so that they are not adversely affected by, for example, irregular food consumption or exercise. In addition, a physician dealing with a particular diabetic individual requires detailed information on the lifestyle of the individual to provide effective treatment or modification of treatment for controlling diabetes. Currently, one of the ways of monitoring the lifestyle of an individual with diabetes has been for the individual to keep a paper logbook of their lifestyle, and to test their blood glucose on a regular basis, particularly before meals, after meals, and when fasting. Another way is for an individual to simply rely on remembering facts about their lifestyle and when they test, and then relay these details to their physician on each visit.

The aforementioned methods of recording lifestyle information are inherently difficult, time consuming, and possibly inaccurate. It's easy to forget to test, and paper logbooks are not always carried by an individual and may not be accurately completed when required. Paper logbooks are small and it is difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distil or separate the component information, and there is no way for a paper logbook to proactively remind a user to test. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

Moreover, a diabetic individual often has to keep a plurality of devices on their person for diagnosis and treatment, for example both glucose level monitoring equipment and medication. Hence, having to carry paper records of their lifestyle and a log of when they test is an added unwanted burden, and entry of data therein is very time consuming.

There currently exist a number of portable electronic devices that can measure glucose levels in an individual and store the levels for recalling or uploading to another computer for analysis. One such device is the Accu-Check™ Complete™ System from Roche Diagnostics, which provides limited functionality for storing lifestyle data. However, the Accu-Check™ Complete™ System only permits a limited selection of lifestyle variables to be stored in a meter. There is a no intelligent feedback from values previously entered into the meter and the user interface is unintuitive for an infrequent user of the meter. In addition, there is no convenient way to remind the user when to test, and to assure that tests are being conducted at appropriate times.

SUMMARY OF THE DISCLOSURE

Applicants have recognized a need for an electronic device that reminds the user when to test and that provides assurance that tests are being conducted and recorded at appropriate times. Such device must be intuitive and easier to use, thereby encouraging an individual to test at appropriate times. Appropriate times should be taken to mean times that are particularly relevant to management of diabetes, and which might affect or represent an individual's physical condition. Examples of appropriate times are before and after food consumption, before and after physical exertion (e.g. exercise), before and after medication intake, and after fasting.

In view of the foregoing and in accordance with one aspect, there is provided a method of operating an analyte measurement device having a display, user interface, processor, memory and user interface buttons, the method can be achieved by measuring an analyte with the analyte measurement device; displaying a value representative of the analyte; prompting a user to activate a test reminder; and activating the test reminder to remind a user to conduct a test measurement at a different time.

In an embodiment, the prompting includes repetitively flashing on the display an icon representative of one of the user interface buttons to prompt a selection of such user interface button.

In an embodiment, the prompting includes illuminating one of the user interface buttons to prompt a selection of such user interface button.

In an embodiment, the method further includes disabling all of the user interface buttons except for one of the user interface buttons.

In an embodiment, the user interface buttons include an up button, a down button, an enter button, and a test reminder button.

In an embodiment, the test reminder includes a before meal test reminder or an after meal test reminder.

In an embodiment, the test reminder includes an after meal test reminder.

In an embodiment, the prompting includes always prompting a user whenever a measuring step has been completed.

In an embodiment, the prompting includes prompting a user whenever a measuring step was taken before a meal.

In an embodiment, the activating includes storing in memory the date and time to display the test reminder.

In an embodiment, the analyte measurement device includes a glucose meter.

In an embodiment, the measuring includes inserting a test strip into a strip port provided by the measurement device; and depositing a blood sample on a testing portion of the test strip without entering a calibration parameter for the test strip.

In an embodiment, the measuring includes inserting a test strip into a strip port provided by the measurement device;

inputting a calibration parameter for the test strip via the user interface buttons of the device; and depositing a blood sample on a testing portion of the test strip.

In an embodiment, the inserting includes turning on the measurement device when the strip is fully inserted into the strip port.

In an embodiment, the plurality of menus to be displayed is selected.

In an embodiment, the plurality of menus includes at least one time for the test reminder.

In view of the foregoing and in accordance with another aspect, there is provided a method of operating an analyte measurement device having a display, user interface, processor, memory and user interface buttons, the method can be achieved by pressing one of the user interface buttons to turn the analyte measurement device on, prompting a user to confirm selection of a test reminder, and pressing one of the user interface buttons to confirm selection of a test reminder.

In an embodiment, the prompting includes repetitively flashing on the display an icon representative of one of the user interface buttons to prompt selection of such user interface button.

In an embodiment, the prompting includes illuminating one of the user interface buttons to prompt a selection of such user interface button.

In an embodiment, the method further includes disabling all of the user interface buttons except for one of the user interface buttons.

In an embodiment, the user interface buttons include an up button, a down button, an enter button, and a test reminder button.

In an embodiment, the test reminder includes a before meal test reminder or an after meal test reminder.

In an embodiment, the test reminder includes an after meal test reminder.

In an embodiment, the confirming includes storing in memory the date and time to display the test reminder.

In an embodiment, the analyte measurement device includes a glucose meter.

In an embodiment, the plurality of menus to be displayed is selected.

In an embodiment, the plurality of menus includes at least one time for the test reminder.

In view of the foregoing and in accordance with another aspect, there is provided an analyte measurement device comprising a housing having: a strip port coupled to an analyte measurement unit; a processor coupled to the analyte measurement unit, a memory, user interface input, and a display driver; a display unit coupled to the display driver; and a plurality of user interface buttons including a test reminder button so that upon activation of the test reminder button, a time and date can be stored in the memory to remind the user to conduct a measurement.

These and other embodiments, features and advantages will become apparent to those skilled in the art when taken with reference to the following more detailed description of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which.

DETAILED DESCRIPTION OF THE FIGURES

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
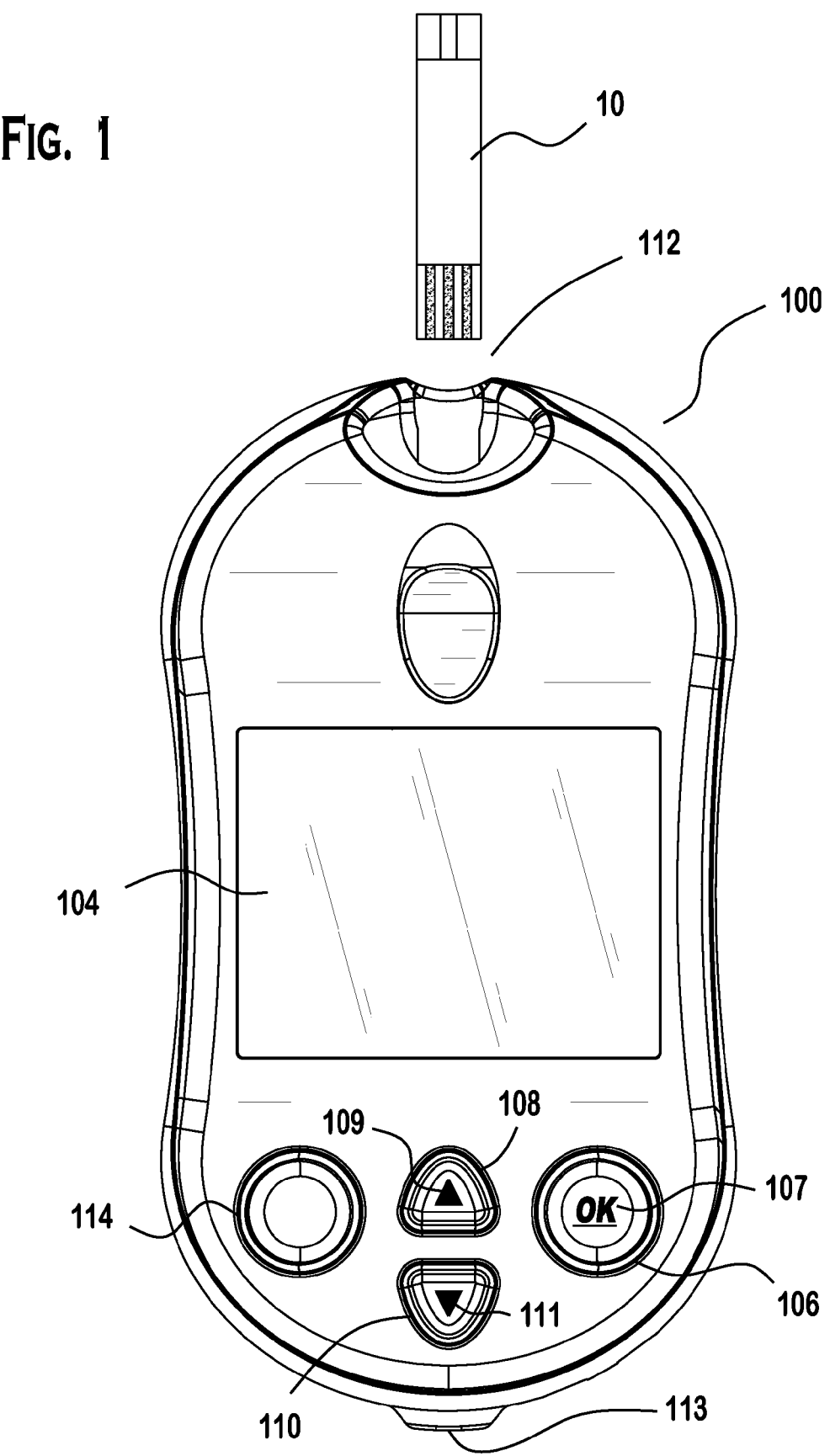
FIG. 1 is an exemplary plan view of an analyte measurement device, according to an embodiment.

FIG. 1 illustrates an analyte measurement device 100, for testing glucose levels in the blood of an individual. Analyte measurement device 100 may include user interface buttons (106, 108, 110, 114) for entry of data, navigation of menus, and execution of commands. Data can include values representative of analyte concentration, and/or information, which are related to the everyday lifestyle of an individual. Information, which is related to the everyday lifestyle, can include food intake, medication use, the occurrence of health check-ups and general health condition and exercise levels of an individual. Analyte measurement device 100 also may include display 104. Display 104 can be used to report measured glucose levels, and to facilitate entry of lifestyle related information.

Analyte measurement device 100 may include first user interface button 106, second user interface button 108, third user interface button 110, and test reminder button 114. User interface buttons 106, 108, and 110 facilitate entry and analysis of data stored in the testing device, enabling a user to navigate through the user interface displayed on display 104. Test reminder button 114 allows test reminders to be set. User interface buttons 106, 108, and 110 include first marking 107, second marking 109, and third marking 111, which help in correlating user interface buttons to characters on display 104. Test reminder button 114 can include markings as well, helping to correlate test reminder button 114 with to characters on display 104.

Analyte measurement device 100 can be turned on by inserting a test strip 10 into strip port 112, by pressing and briefly holding first user interface button 106, or when data traffic is detected across optional data port 113. Analyte measurement device 100 can be switched off by removing the test strip 10, pressing and briefly holding first user interface button 106, navigating to and selecting a meter off option from a main menu screen, or by not pressing any buttons for a predetermined time. Display 104 can optionally include a backlight. The test strip port 112 may include its own light source or the port 112 may share a common light source with the backlight for the display 104.

Data port 113 is optional, and accepts a suitable connector attached to a connecting lead, thereby allowing analyte measurement device 100 to be linked to an external device such as a personal computer. Data port 113 can be any port that allows for transmission of data (serial or parallel) such as, for example, serial or parallel port in wired or wireless form. A personal computer, running appropriate software, allows entry and modification of set-up information (e.g. the current time, date, and language), and can perform analysis of data collected by analyte measurement device 100. In addition, the personal computer may be able to perform advanced analysis functions, and/or transmit data to other computers (i.e. over the internet) for improved diagnosis and treatment. Connecting analyte measurement device 100 with a local or remote computer facilitates improved treatment by health care providers.

Figure 2:
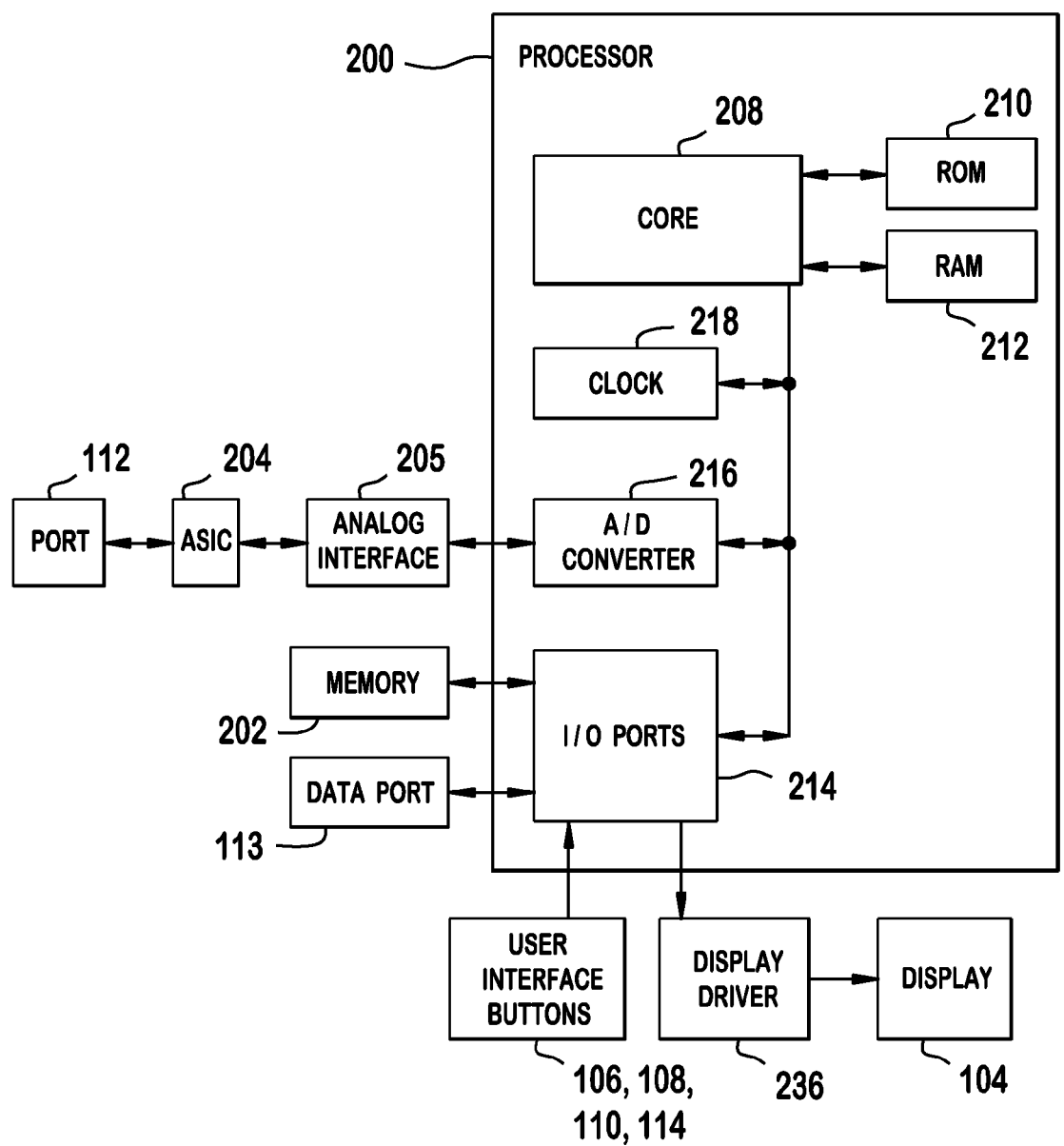
FIG. 2 is an exemplary block diagram illustrating the principal internal components of an analyte measurement device, according to an embodiment.

Referring to FIG. 2, an exemplary internal layout of analyte measurement device 100 is shown. Analyte measurement device 100 may include a processor 200, which in some embodiments described and illustrated herein is a 32-bit RISC microcontroller. The processor can be bi-directionally connected via I/O ports 214 to memory 202, which in some embodiments described and illustrated herein is an EEPROM. Also connected to processor 200 via I/O ports 214 are the data port 113, the user interface buttons 106, 108, 110, and 114, and a display driver 236. Data port 113 can be connected to processor 200, thereby enabling transfer of data between memory 202 and an external device, such as a personal computer. User interface buttons 106, 108, 110, and 114 are directly connected to processor 200. Processor 200 controls display 104 via display driver 236.

In one embodiment, analyte measurement device 100 may include an Application Specific Integrated Circuit (ASIC) 204, providing electronic circuitry used in measurements of glucose level in blood that has been applied to a test strip 10 inserted into strip port 112. Analog voltages can pass to and from ASIC 204 by way of analog interface 205. Analog signals from analog interface 205 can be converted to digital signals by A/D converter 216. Processor 200 further may include core 208, ROM 210 (containing computer code), RAM 212, and clock 218. In one embodiment, the processor 200 is configured (or programmed) to disable all of the user interface buttons except for a single button upon a display of an analyte value by the display unit such as, for example, during a time period after an analyte measurement. In an alternative embodiment, the processor 200 is configured (or programmed) to ignore any input from all of the user interface buttons except for a single button upon a display of an analyte value by the display unit.

Figure 3:
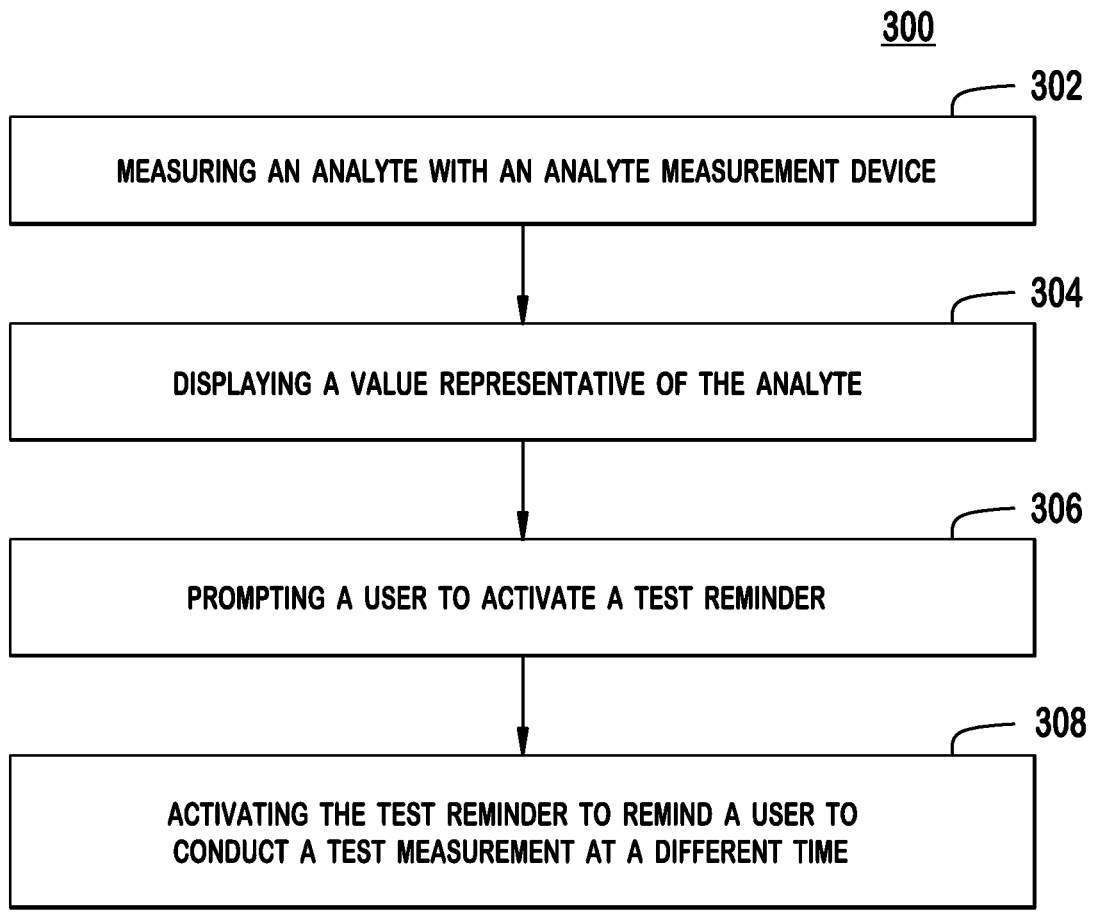
FIG. 3 is an exemplary flow chart illustrating a method of operating an analyte measurement device, according to an embodiment.

FIG. 3 is an exemplary flow chart illustrating a method of operating an analyte measurement device, according to an embodiment described and illustrated herein. Method 300 may include processes 302, 304, 306, and 308. In process 302, an analyte-measuring device measures an analyte. In process 304, the analyte measuring device displays a value representative of the analyte. In process 306, the analyte measuring device prompts the user to activate a test reminder. In process 308, the user activates a test reminder to remind a user to conduct a test measurement at a different time. In any embodiments described and illustrated herein, the analyte measurement device may include a display, a user interface, a processor, a memory and user interface buttons. Prompting may include repetitively flashing on the display an icon representative of one of the user interface buttons to prompt selection of such user interface button. Alternatively, prompting may include illuminating at least one of the user interface buttons to prompt selection of at least one user interface button. It is noted that the reminder is not limited to before meal or after meal but can be utilized any specific time selected by the user, patient or physician.

Figure 4:
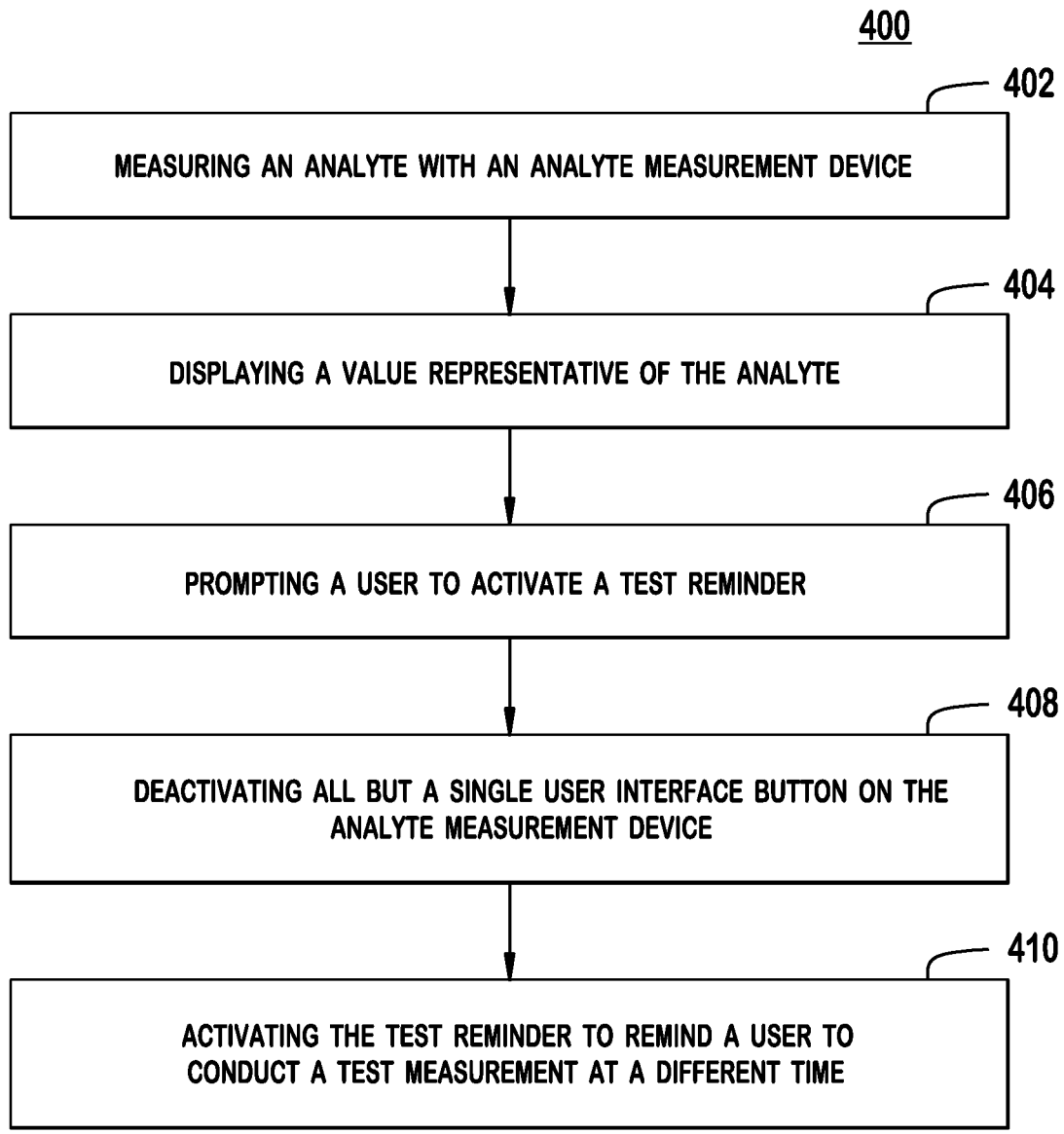
FIG. 4 is an exemplary flow chart illustrating a method of operating an analyte measurement device when only a single user interface button on the analyte measurement device is active, according to an embodiment.

FIG. 4 is an exemplary flow chart illustrating a method of operating an analyte measurement device when only a single user interface button on the analyte measurement device is active, according to an embodiment described and illustrated herein. Method 400 may include processes 402, 404, 406, 408, and 410. In process 402, an analyte-measuring device measures an analyte. In process 404, the analyte measuring device displays a value representative of the analyte. In process 406, the analyte measuring device prompts the user to activate a test reminder. In process 408, the analyte measuring device deactivates all but a single user interface button. In process 410, the user activates the test reminder to remind the user to conduct a test measurement at a different time. User interface buttons may include an "up" button, a "down" button, an "enter" or "OK" button, and a test reminder button. In any embodiments described and illustrated herein, the test reminder can include a before meal test reminder or an after meal test reminder. Alternatively, the test reminder can be an after meal test reminder.

Figure 5:
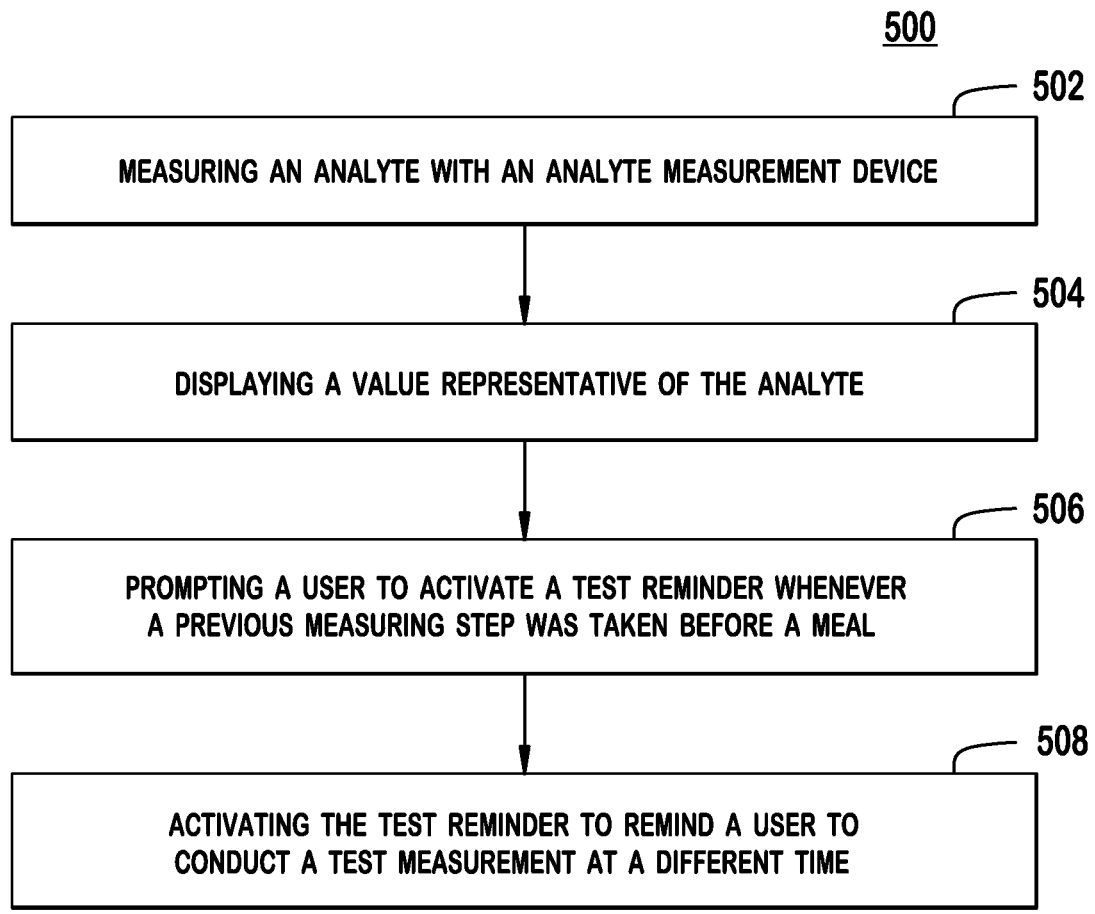
FIG. 5 is an exemplary flow chart illustrating a method of operating an analyte measurement device where a user is prompted to activate a test reminder whenever a previous measuring process was taken before a meal, according to an embodiment.

FIG. 5 is an exemplary flow chart illustrating a method of operating an analyte measurement device where a user is prompted to activate a test reminder whenever a previous measuring process was taken before a meal, according to an embodiment described and illustrated herein. Method 500 may include processes 502, 504, 506, and 508. In process 502, an analyte-measuring device measures an analyte. In process 504, the analyte measuring device displays a value representative of the analyte. In process 506, the analyte measuring device prompts the user to activate a test reminder whenever a previous measuring process was taken before a meal. In process 508, the user activates a test reminder to remind the user to conduct a test measurement at a different time. In any embodiments described and illustrated herein, the analyte measuring device may prompt the user to activate a test reminder whenever a measuring process has been completed.

Figure 6:
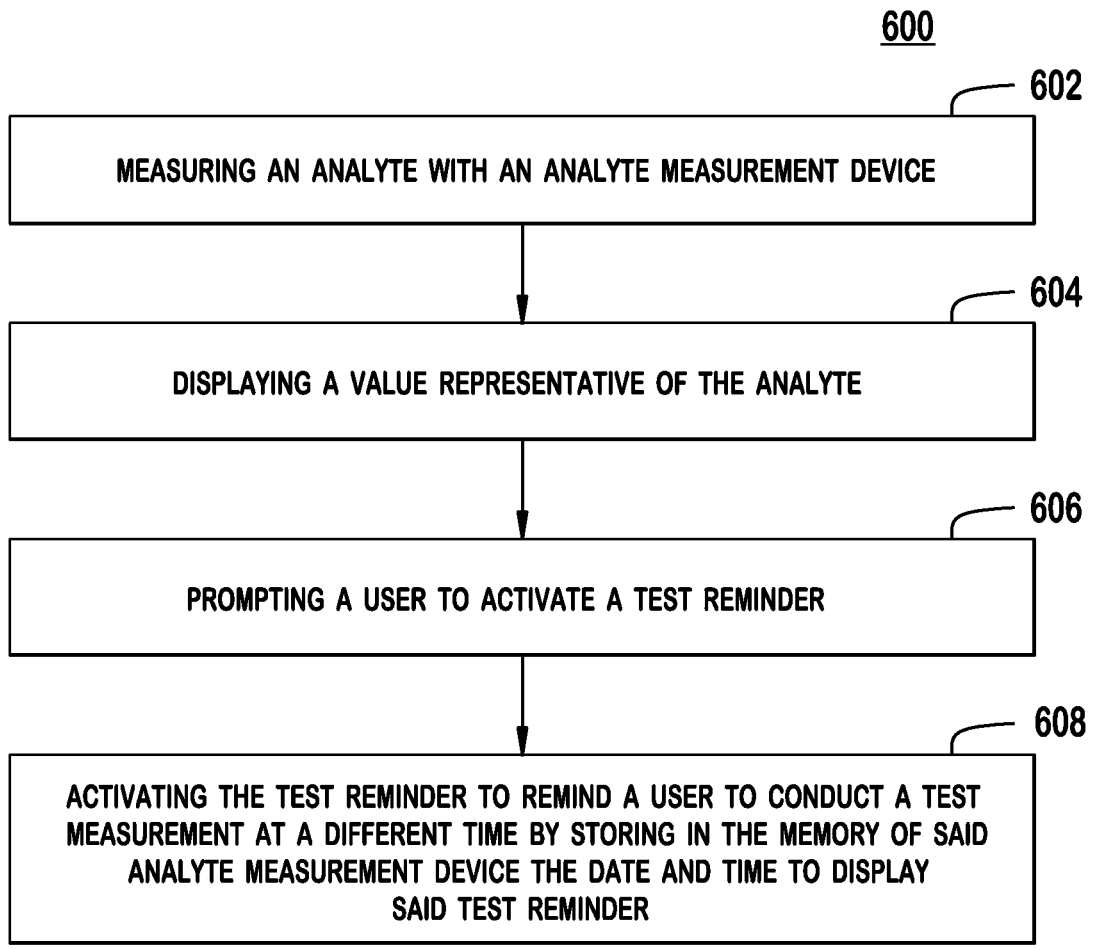
FIG. 6 is an exemplary flow chart illustrating a method of operating an analyte measurement device where the date and time to display a test reminder are stored in the memory of an analyte measurement device, according to an embodiment.

FIG. 6 is an exemplary flow chart illustrating a method of operating an analyte measurement device where the date and time to display a test reminder are stored in the memory of an analyte measurement device, according to an embodiment described and illustrated herein. Method 600 may include processes 602, 604, 606, and 608. In process 602, an analyte-measuring device measures an analyte. In process 604, the analyte measuring device displays a value representative of the analyte. In process 606, the analyte measuring device prompts the user to activate a test reminder. In process 608, the user activates a test reminder to remind the user to conduct a test measurement at a different time by storing in the memory of the analyte measurement device the date and time to display the test reminder. In any embodiments described and illustrated herein, the analyte measuring device may include a glucose meter.

Figure 7:
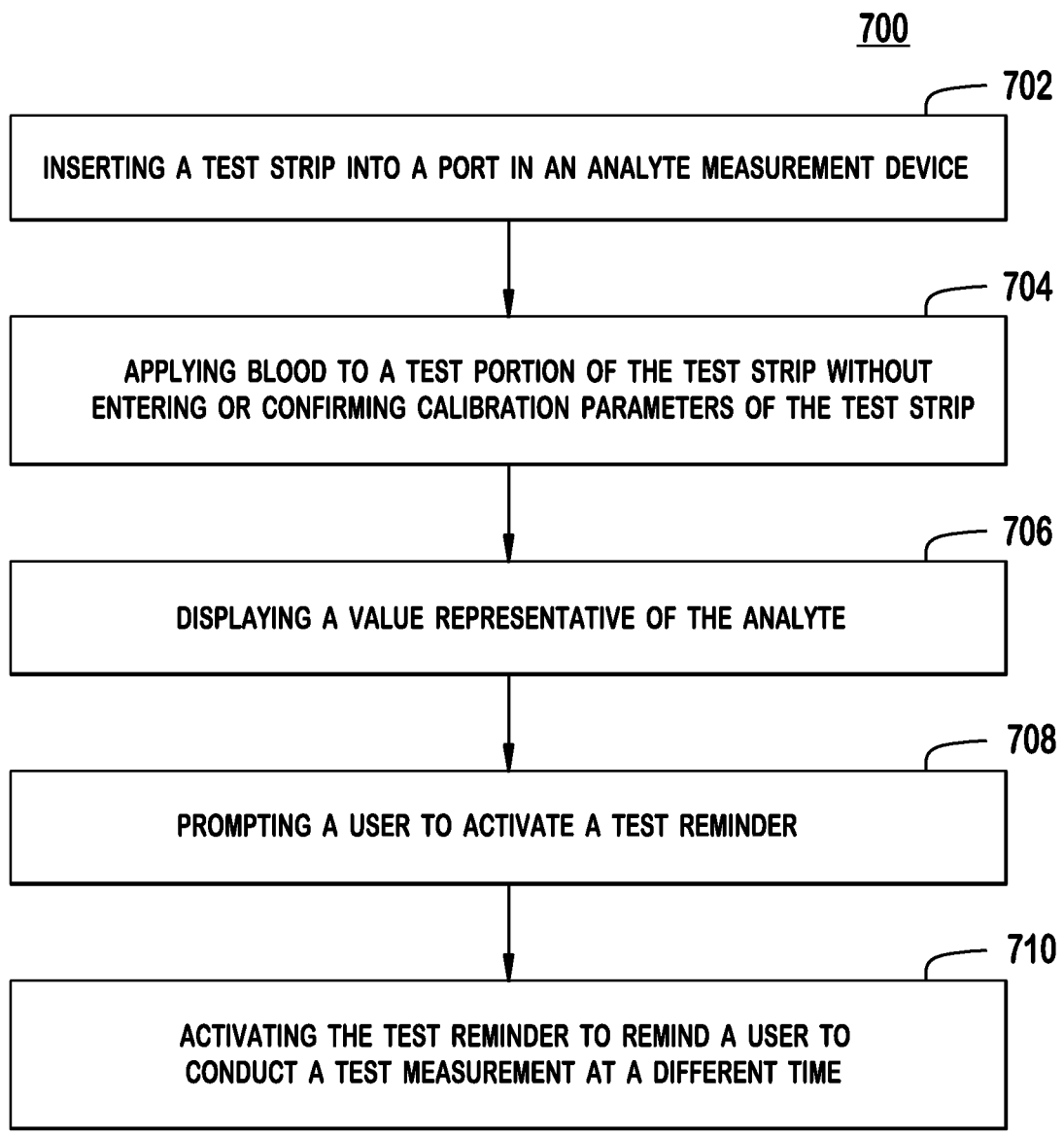
FIG. 7 is an exemplary flow chart illustrating a method of operating an analyte measurement device after inserting a test strip into a strip port in the analyte measurement device, according to an embodiment.

FIG. 7 is an exemplary flow chart illustrating a method of operating an analyte measurement device after inserting a test strip 10 into a strip port 112 in the analyte measurement device, according to an embodiment described and illustrated herein. Method 700 may include processes 702, 704, 706, 708, and 710. In process 702, a test strip 10 is inserted into a strip port in an analyte measurement device. In process 704, blood is applied to a test portion (the portion distal from the strip port 112) of the test strip 10 without entering or confirming calibration parameters of the test strip 10. In process 706, the analyte measuring device displays a value representative of the analyte. In process 708, the analyte measuring device prompts the user to activate a test reminder. In process 710, the user activates a test reminder to remind the user to conduct a test measurement at a different time. In any embodiments described and illustrated herein, measuring may include: inserting a test strip 10 into a strip port in the analyte measurement device, then depositing a sample of blood on a testing portion of the test strip 10 without entering a calibration parameter for the test strip 10.

Figure 8:
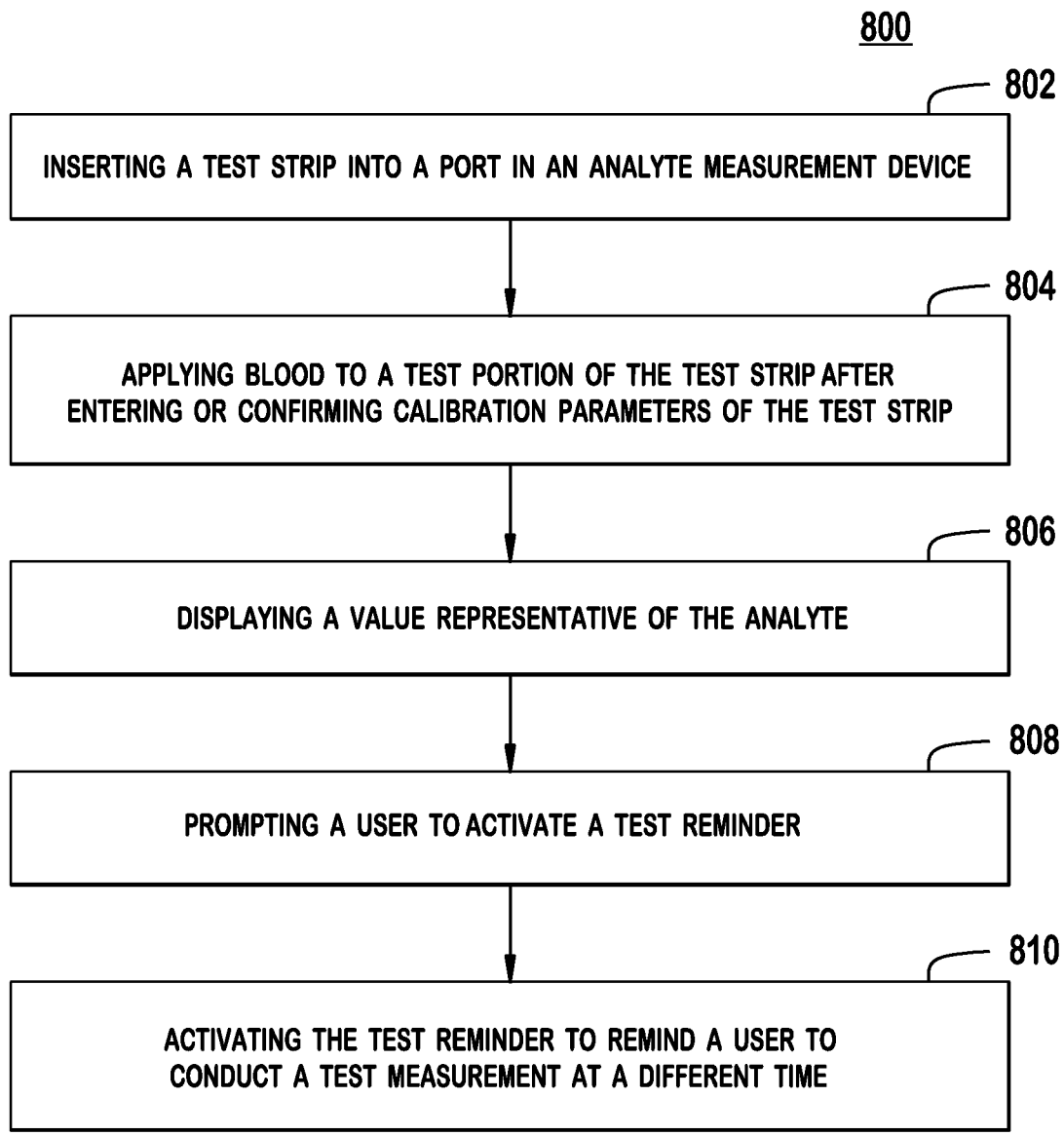
FIG. 8 is an exemplary flow chart illustrating a method of operating an analyte measurement device after inserting a test strip into a strip port in the analyte measurement device and either entering or confirming calibration parameters of the test strip, according to an embodiment.

FIG. 8 is an exemplary flow chart illustrating a method of operating an analyte measurement device after inserting a test strip 10 into a strip port in the analyte measurement device and either entering or confirming calibration parameters of the test strip 10, according to an embodiment described and illustrated herein. Method 800 may include processes 802, 804, 806, 808, and 810. In process 802, a test strip 10 is inserted into a strip port in an analyte measurement device. In process 804, blood is applied to a test portion of the test strip 10 after entering or confirming calibration parameters of the test strip 10. In process 806, the analyte measuring device displays a value representative of the analyte. In process 808, the analyte measuring device prompts the user to activate a test reminder. In process 810, the user activates a test reminder to remind the user to conduct a test measurement at a different time. In any embodiments described and illustrated herein, the measuring may include: inserting a test strip 10 into a strip port in the measurement device; inputting a calibration parameter for the test strip 10 via the user interface buttons of the device; and depositing a blood sample on a testing portion of the test strip 10.

Figure 9:
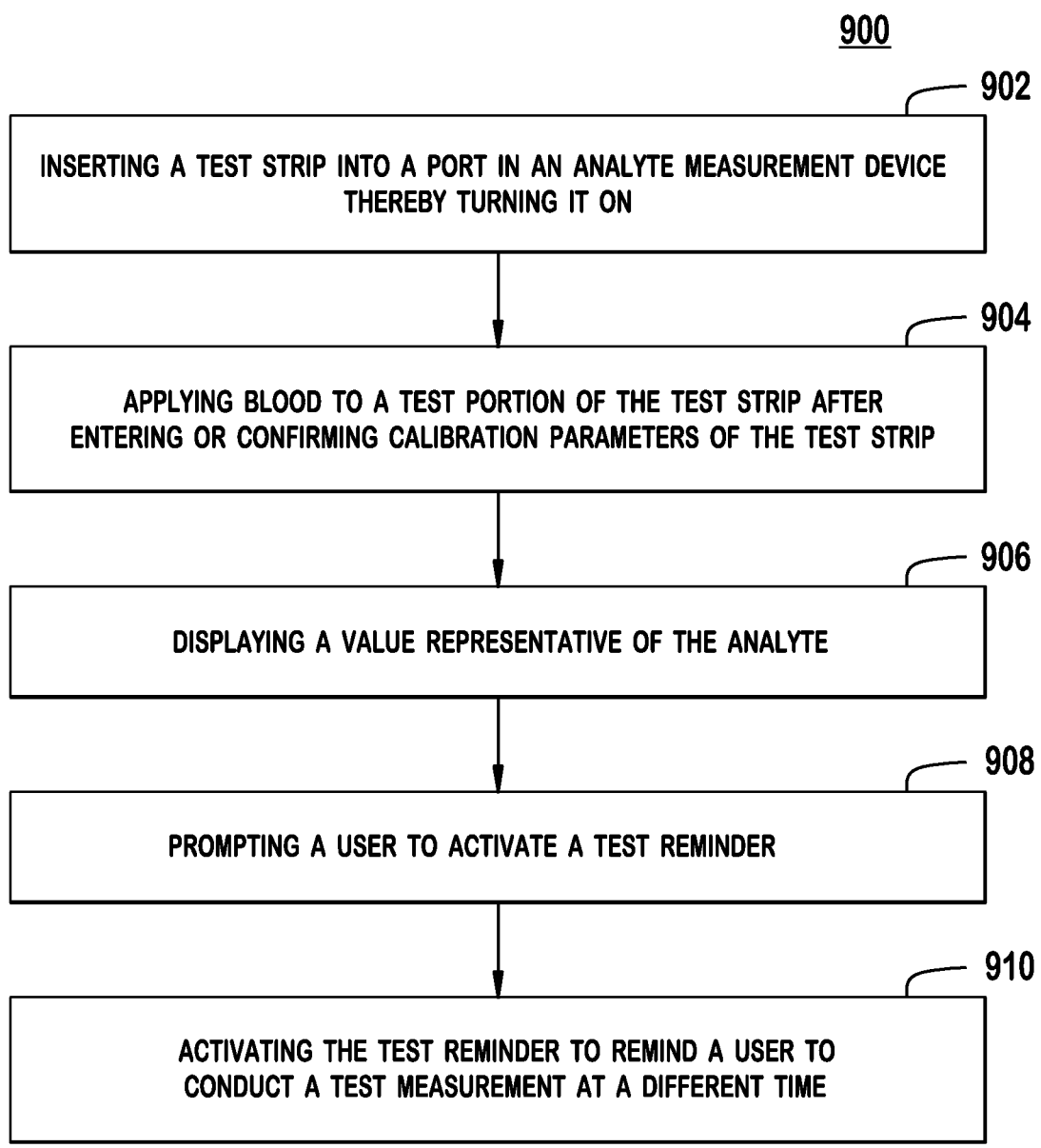
FIG. 9 is an exemplary flow chart illustrating a method of operating an analyte measurement device after inserting a test strip into a strip port in the analyte measurement device thereby turning the analyte measurement device on, according to an embodiment.

FIG. 9 is an exemplary flow chart illustrating a method of operating an analyte measurement device after inserting a test strip 10 into a strip port in the analyte measurement device thereby turning the analyte measurement device on. Method 900 may include processes 902, 904, 906, 908, and 910. In process 902, a test strip 10 is inserted into a strip port in an analyte measurement device, thereby turning it on. In process 904, blood is applied to a test portion of the test strip 10 without entering or confirming calibration parameters of the test strip 10. In process 906, the analyte measuring device displays a value representative of the analyte. In process 908, the analyte measuring device prompts the user to activate a test reminder. In process 910, the user activates a test reminder to remind the user to conduct a test measurement at a different time. In any embodiments described and illustrated herein, inserting may include turning on the measurement device when the strip is fully inserted into the strip port. Alternatively, a plurality of menus may be displayed. In a further embodiment, one of a plurality of menus may include at least one amount of elapsed time for the test reminder.

Figure 10:
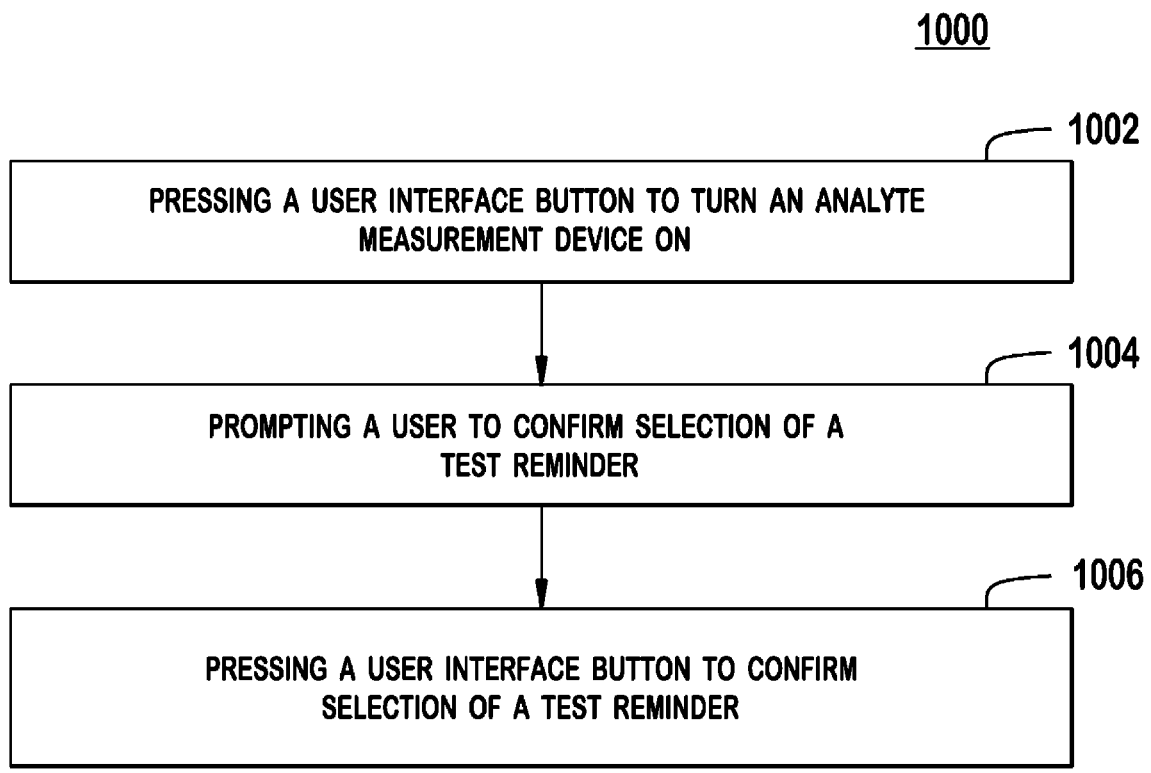
FIG. 10 is an exemplary flow chart illustrating a method of operating an analyte measurement device where the analyte measurement device is turned on by pressing a user interface button, a user is prompted to confirm selection of a test reminder, and a user interface button is pressed to confirm selection of a test reminder, according to an embodiment.

FIG. 10 is an exemplary flow chart illustrating a method of operating an analyte measurement device where the analyte measurement device is turned on by pressing a user interface button, a user is prompted to confirm selection of a test reminder, and a user interface button is pressed to confirm selection of a test reminder. Method 1000 may include processes 1002, 1004, and 1006. In process 1002, the user presses a user interface button to turn the analyte measurement device on. In process 1004, the analyte measuring device prompts the user to confirm selection of a test reminder. In process 1006, the user presses a user interface button to confirm selection of a test reminder. In any embodiments described and illustrated herein, prompting may include repetitively flashing on the display an icon representative of a single user interface button to prompt selection of the single user interface button. Alternatively, prompting may include illuminating at least one of the user interface buttons to prompt selection of at least one user interface button.

Figure 11:
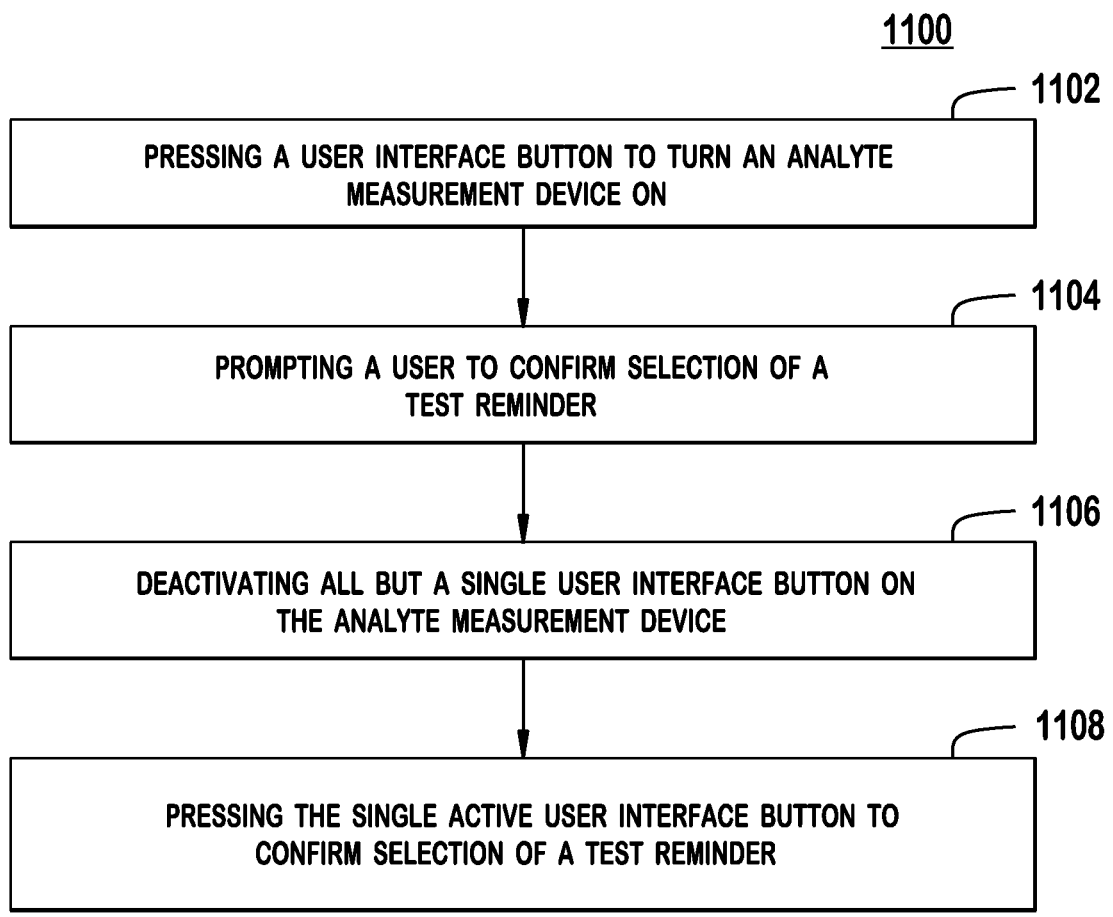
FIG. 11 is an exemplary flow chart illustrating a method of operating an analyte measurement device when only a single user interface button on the analyte measurement device is active, according to an embodiment.

FIG. 11 is an exemplary flow chart illustrating a method of operating an analyte measurement device when only a single user interface button on the analyte measurement device is active. Method 1100 may include processes 1102, 1104, 1006, and 1108. In process 1102, the user presses a user interface button to turn the analyte measurement device on. In process 1104, the analyte measuring device prompts the user to confirm selection of a test reminder. In process 1106, all but a single user interface button on the analyte measurement device are deactivated. In process 1108, the user presses the single activated user interface button to confirm selection of a test reminder. In any embodiments described and illustrated herein, the user interface buttons may include an up button, a down button, an enter button, and a test reminder button. Alternatively, the test reminder may include a before meal test reminder or an after meal test reminder. In a further embodiment, the test reminder may include an after meal test reminder.

Figure 12:
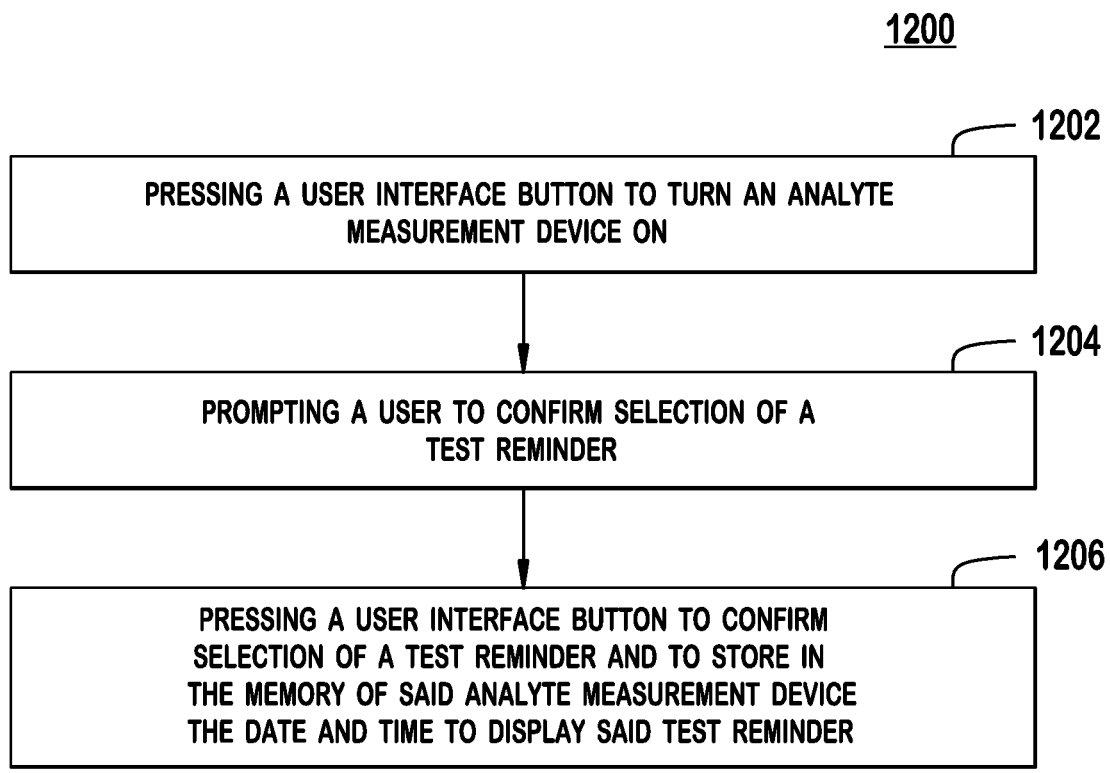
FIG. 12 is an exemplary flow chart illustrating a method of operating an analyte measurement device where the date and time to display a test reminder are stored in the memory of an analyte measurement device, according to an embodiment.

FIG. 12 is an exemplary flow chart illustrating a method of operating an analyte measurement device where the date and time to display a test reminder are stored in the memory of an analyte measurement device. Method 1200 may include processes 1202, 1204, and 1206. In process 1202, the user presses a user interface button to turn the analyte measurement device on. In process 1204, the analyte measuring device prompts the user to confirm selection of a test reminder. In process 1206, the user presses the single activated user interface button to confirm selection of a test reminder and to store in the memory of said analyte measurement device the date and time to display said test reminder. The analyte measurement device may include a glucose meter. Alternatively, the method may further include selecting a plurality of menus to be displayed. In a further alternative, the plurality of menus may include at least one elapsed time for the test reminder.

Figure 13:
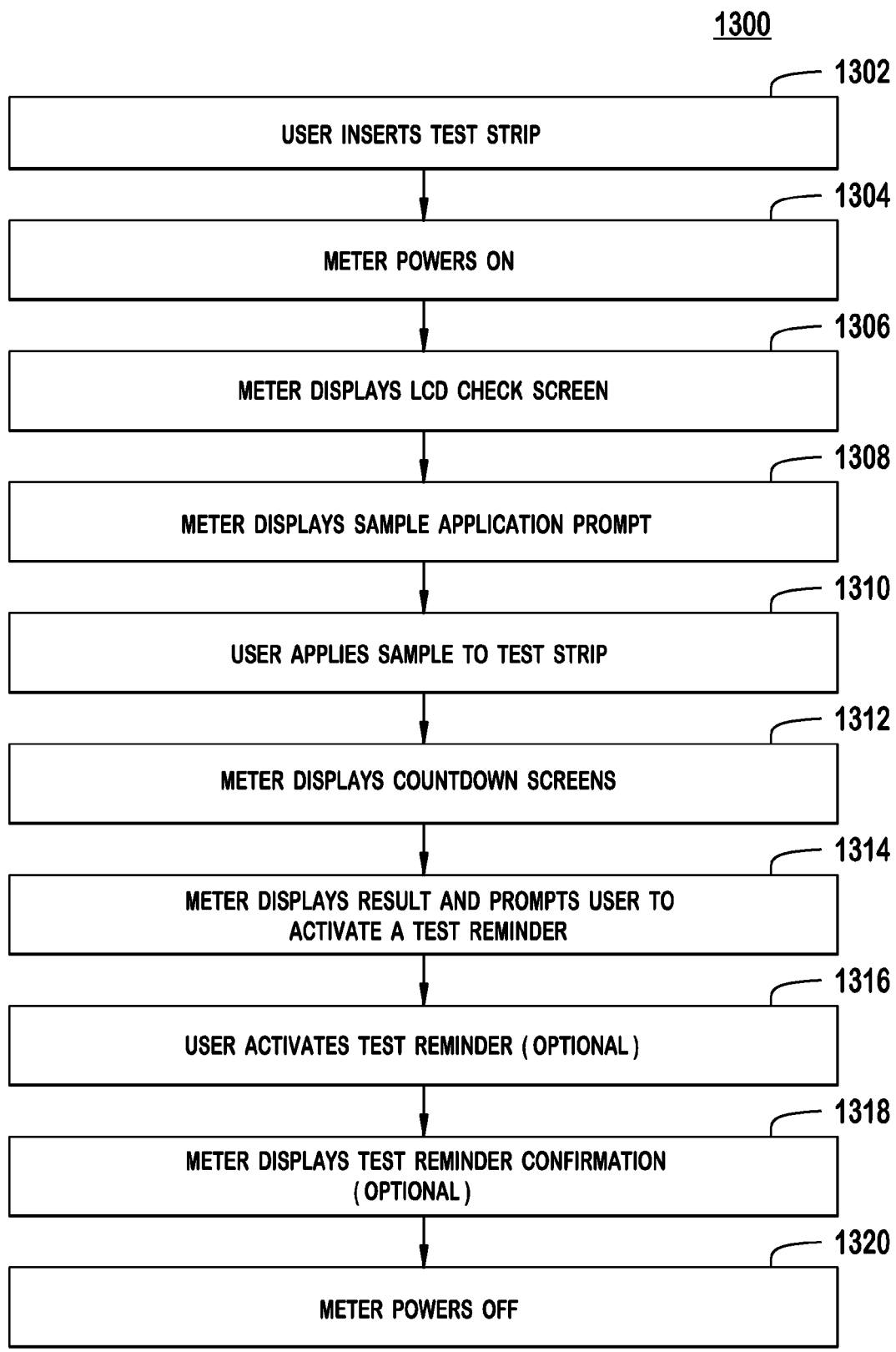
FIG. 13 is an exemplary flow chart illustrating a method of operating an analyte measurement device and actions taken by the analyte measurement device, according to an embodiment.

FIG. 13 is an exemplary flow chart illustrating a method of operating an analyte measurement device and actions taken by the analyte measurement device. Method 1300 may include processes 1302, 1304, 1306, 1308, 1310, 1312, 1314, 1316, 1318, and 1320. In process 1302, a user inserts a test strip 10 into a strip port in an analyte measurement device. In process 1304, the analyte measuring device turns on. In process 1306, the analyte-measuring device displays an LCD check screen. In process 1308, the analyte measuring device displays a sample application prompt. In process 1310, the user applies sample to the test strip 10. In process 1312, the analyte measuring device displays a series of countdown screens. In process 1314, the analyte measuring device displays a value representative of the analyte and prompts the user to activate a test reminder. In process 1316, the user optionally activates a test reminder, causing the date and time for the test reminder to be displayed to be stored in the memory of the analyte measurement device. In process 1318, the analyte measurement device optionally displays a test reminder confirmation. In process 1320, the analyte measurement device turns off after a predetermined time, with or without interaction from the user.

In conclusion, the testing device and methods described and illustrated herein significantly reduce obstacles associated with blood glucose testing. Thus the present invention promotes frequent monitoring for diabetic individuals by providing a simple, efficient way of reminding a user to test. By testing in the manner described herein, it is easier for a user to establish proper testing frequency, and provide vital information to health care practitioners.

While the invention has been described in terms of particular variations and illustrative figures, those of ordinary skill in the art will recognize that the invention is not limited to the variations or figures described. In addition, where methods and process described above indicate certain events occurring in certain order, those of ordinary skill in the art will recognize that the ordering of certain process may be modified and that such modifications are in accordance with the variations of the invention. Additionally, certain of the process may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of operating an analyte measurement device having a display, user interface, processor, memory and user interface buttons, the method comprising:

measuring an analyte with the analyte measurement device;

displaying a value representative of the analyte on the display of the device;

after the displaying step, prompting a user to activate a test reminder;

activating a user interface button of the device to activate the test reminder for a user to conduct a test measurement at a different time; and the device disabling all of the user interface buttons except for the user interface button used for activation of the test reminder.

2. The method of claim 1, in which the prompting comprises repetitively flashing on the display an icon representative of one of the user interface buttons to prompt a selection of such user interface button.

3. The method of claim 1, in which the prompting comprises illuminating one of the user interface buttons to prompt a selection of such user interface button.

4. The method of claim 1, in which the user interface buttons comprise an up button, a down button, an enter button, and a test reminder button.

5. The method of claim 1, in which the test reminder comprises at least one of a before meal test reminder or an after meal test reminder.

6. The method of claim 5, in which the test reminder comprises an after meal test reminder.

7. The method of claim 1, in which the prompting comprises always prompting a user whenever a measuring step has been completed.

8. The method of claim 1, in which the prompting comprises prompting a user whenever a previous measuring step was taken before a meal.

9. The method of claim 1, in which the activating comprises storing in memory the different time including a date to display the test reminder.

10. The method of claim 1, in which the analyte measurement device comprises a glucose meter.

11. The method of claim 1, in which the measuring comprises:

inserting a test strip into a strip port provided by the measurement device; and depositing a blood sample on a testing portion of the test strip without entering a calibration parameter for the test strip.

12. The method of claim 1, in which the measuring comprises inserting a test strip into a strip port provided by the measurement device;

inputting a calibration parameter for the test strip via the user interface buttons of the device; and depositing a blood sample on a testing portion of the test strip.

13. The method of claim 1, in which the inserting comprises turning on the measurement device when the strip is fully inserted into the strip port.

14. The method of claim 1, further comprising selecting a plurality of menus to be displayed.

15. The method of claim 14, in which the plurality of menus comprise at least one time for the test reminder.

* * * * *